(12) United States Patent
Pham et al.

(10) Patent No.: US 8,012,186 B2
(45) Date of Patent: Sep. 6, 2011

(54) UNIPLANAR SCREW

(75) Inventors: Khiem Pham, Chalfont, PA (US); Andrew Iott, Villanova, PA (US)

(73) Assignee: Globus Medical, Inc., Audubon, PA (US)

( * ) Notice: Subject to any disclaimer, the term of this patent is extended or adjusted under 35 U.S.C. 154(b) by 445 days.

(21) Appl. No.: 12/249,418

(22) Filed: Oct. 10, 2008

(65) Prior Publication Data

US 2010/0094343 A1   Apr. 15, 2010

(51) Int. Cl.
*A61B 17/70* (2006.01)
(52) U.S. Cl. ...................................... 606/265
(58) Field of Classification Search .......... 606/265, 606/266, 267, 270, 272, 308
See application file for complete search history.

(56) References Cited

U.S. PATENT DOCUMENTS

| 6,280,442 | B1 * | 8/2001 | Barker et al. ............... 606/60 |
| 7,875,065 | B2 * | 1/2011 | Jackson ..................... 606/305 |
| 2004/0225289 | A1 * | 11/2004 | Biedermann et al. ......... 606/61 |

* cited by examiner

*Primary Examiner* — Todd E Manahan
*Assistant Examiner* — Elana B Fisher

(57) ABSTRACT

A spinal stabilization system for surgical implantation in the spine having a bone fastener. The bone fastener is provided with a head portion and a shaft portion. A housing is also provided with a recess defined by sidewalls and an opening for receiving the head portion of the bone fastener. A seating element is disposed within the housing and positioned over the head portion of the bone fastener. An elongate rod is positioned on the seating element within the recess of the housing. The system also includes a cap capable of engaging with a top portion of the housing and capturing the elongate rod within the recess of the housing when the cap is rotated. The bone fastener articulates in a single plane with respect to the housing and the seat element.

6 Claims, 6 Drawing Sheets

UNIPLANAR SCREW

FIELD OF THE INVENTION

The present invention relates to orthopedic fixation device comprising a rod and a bone screw having a uniplanar screw head. The screw head prevents polyaxial movement and provides locking mechanics to securely prevent movement of the rod within the screw head.

BACKGROUND OF THE INVENTION

Many types of spinal irregularities cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment of these spinal irregularities of involves using a system of pedicle screws and rods to attain stability between spinal segments. Instability in the spine can create stress and strain on neurological elements, such as the spinal cord and nerve roods. In order to correct this, implants of certain stiffness can be implanted to restore the correct alignment and portion of the vertebral bodies. In many cases, an anchoring member such as a pedicle screw along with vertical solid member can help restore spinal elements to a pain free situation, or at least may help reduce pain or prevent further injury to the spine.

It is well known that difficulties can arise during a surgical procedure when attempting to connect a vertical solid member, such as a rod, to a bone screw. As a result, it may be desirable to use a variable angled coupling element to connect a rod to a bone screw. This lessens the need to modify the system such as by bending the rod, by repositioning the screw, or the like. The coupling element acts as an elbow which can reach out to the rod and allow for easier adjustment and installation of the rod in the patient.

Typically, a conventional polyaxial screw often has a cap of some kind used to compress the rod onto the coupling element. This compression of the rod enables the locking mechanism within the coupling element to fix the angle between bone screw and said element. Although polyaxial screw systems are prevalent, the polyaxial screw also cause some issues during placement. For instance, the polyaxial screw system allows a full range of motion that makes it difficult to place correctly within the bony elements of the spine. Furthermore, the accuracy required by the doctor to position the polyaxial screw is paramount and fluctuations due to the mechanical aspects of the polyaxial screw may compromise the accuracy in positioning of the polyaxial screw. Thus, there is a need for a screw system that limits the motion of the screw system during placement of the screw and provides superior fixation in the bony elements of the spine.

SUMMARY OF THE INVENTION

The present invention provides a spinal stabilization system having an elongate rod, and bone fastener with a head and a shaft. A housing with sidewalls defining a recess that is capable of receiving the fastener and elongate rod is further disclosed. Within the housing, a seating element is disposed and positioned over the head portion of the bone fastener. A cap is provided which is capable of engaging with a top portion of the housing and capturing the elongate rod within the recess of the housing. When the cap is rotated within the housing and tightened with a set screw, the rod is compressed about the seating element which locking the fastener. The bottom portion of the head of the fastener is generally rectangular shape and the top portion is curved, and disposed within the housing. The seating element is affixed over the curved top portion of the head and communicates with the head portion to allow motion in a uniplanar direction until the cap and set screw compress upon the elongate rod to lock the fastener into position.

DETAILED DESCRIPTION OF THE ILLUSTRATED EMBODIMENTS

Each of the embodiments described below and in the associated figures describes a uniplanar screw system for use with an orthopedic rod. While the embodiments are described and illustrated as having a screw that has a head and a shaft that extends from the head, it should be understood that other fasteners or securing elements may also be used such as, for example, lamina hooks and sacral blocks. Thus, the present invention may be used with a wide variety of fasteners or securing elements in addition to a bone screw as described herein.

Figures 1, 2:
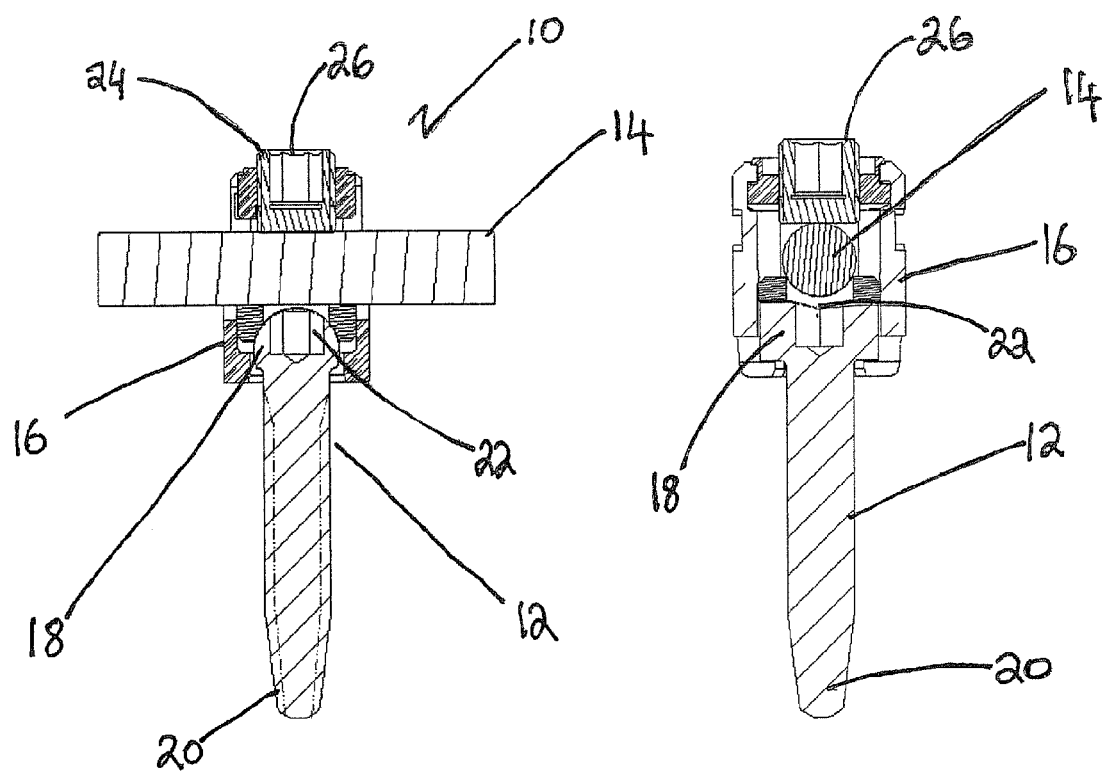
FIG. 1 is the screw and rod system according to an exemplary embodiment of the present invention.
FIG. 2 is another view of the embodiment of the present invention illustrated in FIG. 1.

FIGS. 1 and 2 illustrate a front and side view of a spinal fixation system 10 according to the present invention. The system 10 includes a fastener 12, an elongate rod 14 and a housing 16. The fastener 12 is provided with a head portion 18 and a shaft 20. The head portion 18 is disposed within a bottom portion of the housing 16. The shaft 20 of the fastener 12 is tapered relative to the head portion 18 of the fastener 12 and extends outward from the housing 16. The shaft 20 may be configured with any pitch thread, although, skilled artisans would recognize that other shaft designs would be compatible with the invention. Thus, the physician is free to select from a variety of shaft features, such as thread pitch, shaft diameter to thread diameter ratio, overall shaft shape, and the like according to the conditions of the individual patient's bone.

The head 18 of the fastener 12 is cylindrical in shape to allow the fastener 12 to be adjustable in the uniplanar direction. This preferred configuration also allows the seating element to more securely grip the head. In addition, the head 18 may have an engagement surface that can be engaged by a screw driving tool or other device and, it is preferable that the engagement surface does not disrupt the functionality of the curved surface. The screw head will be discussed in greater detail with reference to FIGS. 6 and 7.

The diameter of the head 18 may be approximately the same as the largest diameter of the shaft 20. The neck may be tapered to provide greater curvature of the head 18 in order to provide a greater variety of angles and positions in which the housing and fastener 12 may be arranged. It should be noted that in other embodiments, the diameter of the shaft 20 can be less than or greater than the diameter of the head 18 and the neck may be un-tapered or differently tapered.

The head 18 also may have an engagement surface 22 that permits the physician to apply torsional or axial forces to the screw with a wrench or screw driving tool to drive the screw into the bone. For instance, the engagement surface 22 of the head 18 may be a polygonal recess in which the head of a tool can engage. For instance, the head 18 may have a hexagonal recess that receives a hexagonal tool such as an Allen wrench. The engagement surface 22 can be configured with a protruding engagement surface 22 that likewise may engage with a tool or device having a corresponding recess, although preferably the protruding engagement surface would not significantly interfere with the capability to vary the angle of the coupling element with respect to the screw.

The elongate rod 14 is positioned in the recess of the housing 16. Specifically, the housing 16 is configured with a U-shaped or wedge shaped seat against which the elongate rod 14 will be locked. The upper portion of the housing is configured with slots, recesses or detents to receive a cap 24. The cap 24 may have corresponding protrusions or slots that permit the cap 24 to engage with and rotate with respect to the housing 16. In one embodiment, rotation of the cap 24 causes it to move downward and toward the screw, thereby applying a downward force against the elongate rod to hold it securely in place. A set screw 26 disposed in the cap 24 may then apply additional downward pressure on the elongate rod to hold it firmly in position.

In an alternative embodiment, the tines or wedges of the housing may be configured to have a tapered or ramped surface that causes gradually increasing radial interference with the cap 24. As the radial forces resulting from this interference increases, the tines or wedges may bend of flex radically inward and press against the elongate rod. One or more detents and depressions may be placed on either the cap to hold the cap in a locked position by engaging with each other a desired cap position. Rotation of the cap in the opposite direction likewise causes the elongated rod to become unlocked.

It should also be noted that the housing 16 and/or cap 24 are configured to provide a tactile feel or audible click when the cap 24 reaches the locking position. One advantage of this is that the physician will receive confirmation that the assembly is in a desired position. In addition, the cap 24 and housing 16 may be configured with one or more detents or similar mechanisms to help prevent the cap 24 from inadvertently backing out of either the first or second positions.

Figure 3:
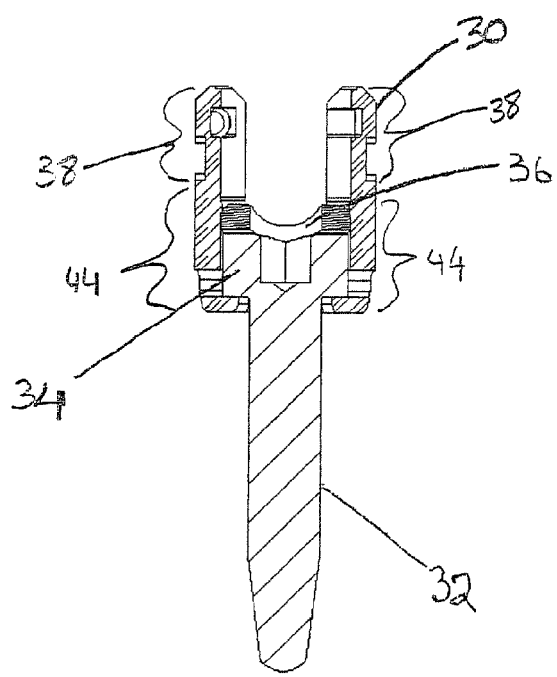
FIG. 3 is a cross-sectional view of the screw system according to the present invention.

It should be noted that the sidewalls of the housing 16 are substantially parallel to each other and provided with a channel for receiving the elongate rod. The outer portion of the sidewalls of the housing 16 are provided with a indentation on either side for receiving an instrument for possible removal of the screw system. As shown in FIG. 3, these indentations may be slotted but the invention is not limited to this configuration. The indentations may be dimensioned to be any size and shape that may be coupled to an instrument for removing the screw fastener and housing. As mentioned above, the inner portion of the side walls are provided with detents, notches, and/or threads are receiving a cap.

Now turning to FIGS. 3 and 4, the relationship and geometry of the housing 30 and fastener 32 will be discussed in greater detail. FIG. 3 shows the housing 30 configured and dimensioned to retain the head 34 of the fastener and a seating element 36. The upper portion 38 of the housing 30, the sidewalls, are provided with a means for a receiving a cap (not shown). The sidewalls are provided indents to receive a portion a protrusion configured on the cap portion. As a result, the housing 30 and the cap may are adapted to be mate with each other.

Figure 4:
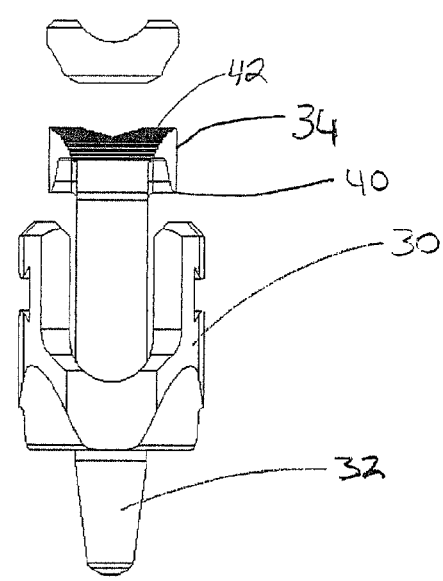
FIG. 4 illustrates the components of the screw system according to the present invention.

FIG. 4 illustrates a more detailed view of the components of the present invention. As seen in FIG. 4, the head portion 34 of the fastener is dimensioned with rectangular shaped bottom 40 portion and a curved top portion 42. The bottom portion 40 of the head is fitted into bottom portion 44 of the housing which is configured and dimensioned so that it mirrors the rectangular shaped bottom portion of the head of the fastener thereby limiting the movement of the shaft of the screw in one direction. Although the rectangular dimensioned bottom portion of the head and the bottom portion of the housing is preferred, both the head and the housing 30 may be provided with any geometry that is configured to be substantially parallel.

Figure 5:
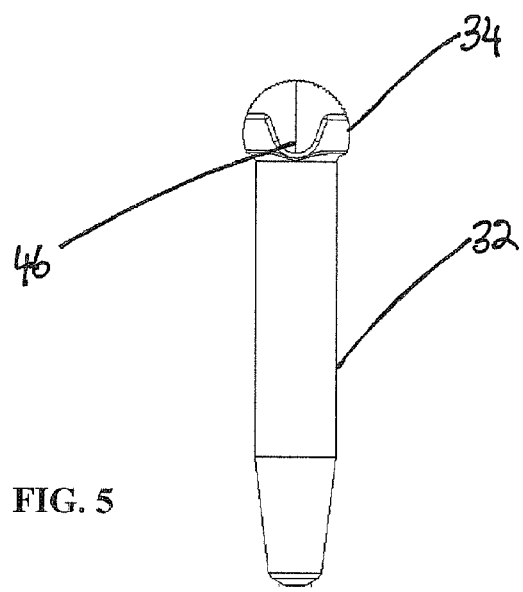
FIG. 5 illustrates the screw portion of the screw system according to the present invention.
Figure 6:
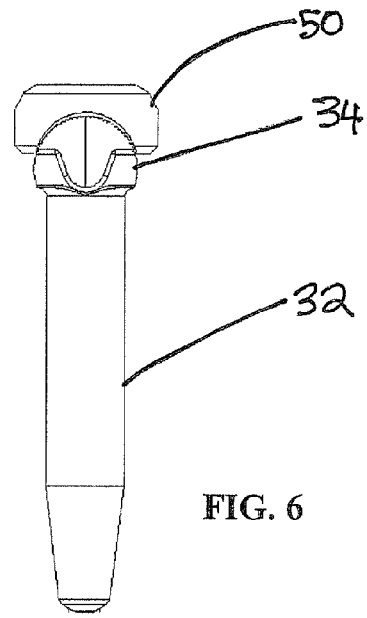
FIG. 6 illustrates the screw portion and the seating element of the screw system according to the present invention.
Figure 7:
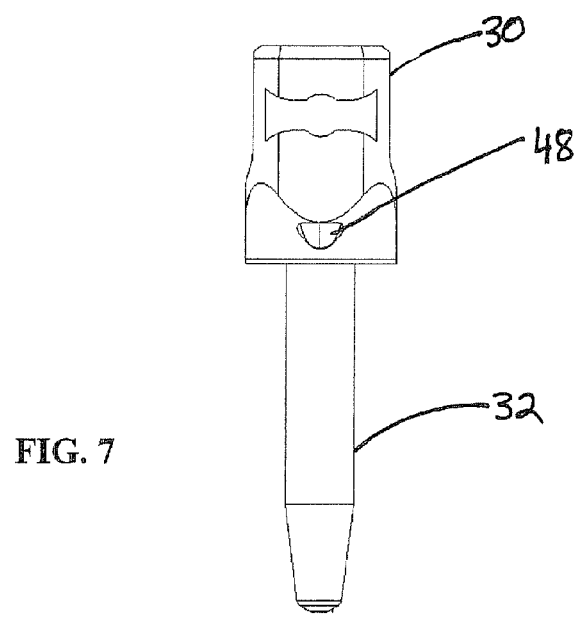
FIG. 7 illustrates the side view of the screw system according to the present invention.

Now, turning to FIGS. 5, 6, and 7, the head 34 of the fastener is provided with slight protrusions 46 that are fitted into an aperture 48 in the sidewalls of the housing 30. Once the protrusions 46 which are on opposite sides of the cylindrical portion of the head are seated within the apertures 48 of the housing, the protrusions 46 and the aperture 48 in combination forms a hinge so that the fastener is displaceable along the rectangular shaped bottom portion 44 of the housing 30. It should be noted that the fastener is only displaceable along the pathway provided by the bottom portion 44 of the housing. It should also be noted that in the preferred embodiment multiple protrusions are used to provide a hinge-type mechanism, however, a single protrusion may be used.

FIG. 6 illustrates rod seating element 50 in conjunction with the fastener. The seating element 50 is configured to be positioned over the curved top portion 34 of the head in a male/female mating orientation. The seating element 50 is elliptical in shape and the top portion of the seating element is provided with a groove wherein the elongate rod may rest. It should be noted that the top seating portion may be dimensioned and/or configured to receive any size or/type of elongate structure. The seating element 36 is fit precisely within the housing and allows the head portion of the fastener to displace within its bottom portion. The curved portion of the head which fits into the seating element is provided with a plurality of grooves and/or serrations. These grooves or serrations are provided so that there is greater friction and/or contact between the seating element and the head. As a result, once a surgeon positions the fastener at an optimal angle and/or location and requires that the fastener be locked, the elongate rod is pushed down on the seating element and the grooves and/or serrations will gain additional purchase with the seating element thereby providing a more rigidity to the fastener. The seating element 50 provides a crush lock on the head of the fastener once the elongate rod is positioned on the seating element.

Figure 8:
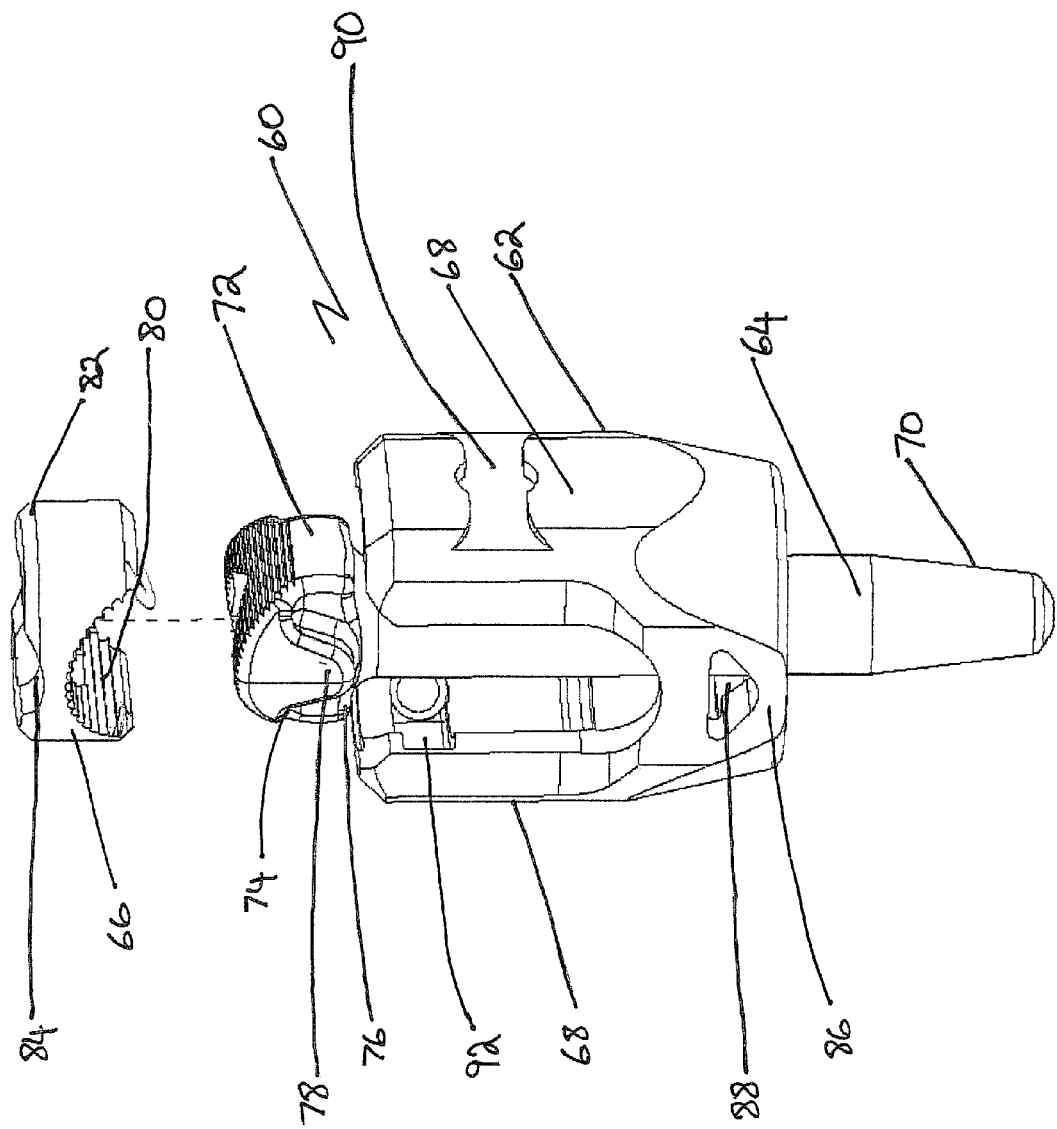
FIG. 8 illustrates the exploded view of the screw system according to the present invention.

FIG. 8 illustrates an exploded view of the components of the fastener system 60 according to the present invention. The spine fastener system 60 includes a housing 62, a fastener 64, a seating element 66 and cap (not shown). The housing 60 is defined with a recess between two sidewalls 68 and an opening at a bottom portion. The fastener 64 is defined with a shaft portion 70 and a head portion 72. The fastener 64 is disposed within the housing 62 so that the shaft portion 70 extends through the opening of the bottom portion of the housing 62. The head portion 72 is provided with a curved top 74 and a quadrangular bottom 76. The head portion 72 is also configured with a slight protrusions 78 on opposite sides. The curved top 74 is in a preferred embodiment is configured with serrations and/or grooves and a recess in a middle portion to receive an instrument.

FIG. 8 further illustrates the rod seating element 66 which is provided with a curved bottom portion 80 and a rod receiving top portion 82. In the preferred embodiment, the rod receiving top portion is grooved 84 so that an elongate rod be precisely fit within the groove 84. However, the groove 84 is not required for the elongate rod to be positioned on top of the rod seating element 66. The rod seating element 66 is dimensioned and configured so that it is located on the bottom portion of the housing 62 and tightly fitted to adapt to the side walls 68. The curved bottom portion 80 of the rod seating element may be roughened or textured to more securely grip the head portion 72 of the fastener 64. The curved bottom surface 80 of the rod seating element 66 may have any type of textures. For instance, the grooves or serrations on the curved bottom surface 80 may match the serrations on the screw head. Thus, the grooves on the curved bottom surface 80 and the grooves on the screw head will cause friction when the screw head is moved, thereby resisting unintended movement or repositioning of the components.

The housing 62, as mentioned above, is provided with sidewalls 68 forming a recess and a bottom portion 86 having an opening for the fastener 64 to extend through. The bottom portion 86 of the housing 62 is provided with apertures 88 on opposing sides of the housing. The protrusions 78 on the head portion 72 of the fastener 64 are fitted into the apertures of on the housing 62. As a result, the fastener 64 is articulatable with respect to the housing 64. More specifically, the head portion 72 articulates with respect to the rod seating element 66 since the protrusions 78 fitted into the apertures 88 function as a hinge. The housing 62 is also provided with grooves 90 on the outer portion of the sidewalls 68 for connecting to an instrument to grip the housing 62 for various purposes. For instance, a rod reducing instrument may be used to grip the housing 62 to reduce the elongate rod within the housing 62 so that is may be precisely seated within the rod seating element 66. The inner portion of the sidewalls are also provided with grooves, detents or another receiving means 92 to receive a portion of a cap having protrusions or grooves. The inner portion may also be threaded so that a threaded cap may be used for locking the rod within the housing 62. The outer portion of the sidewalls 68 may also be threaded to receive a threaded cap. Through the means of cams, wedges, or threads, this invention can place a compression on the head of the screw without use of the elongated rod. The invention further seeks to reduce the number of steps in the procedure, reduce the number of components, and reduce the number of separate pieces associated with the implant. This will reduce intra operative time, create less complicated procedures, and work well in a wider variety of patient anatomy.

Figure 9:
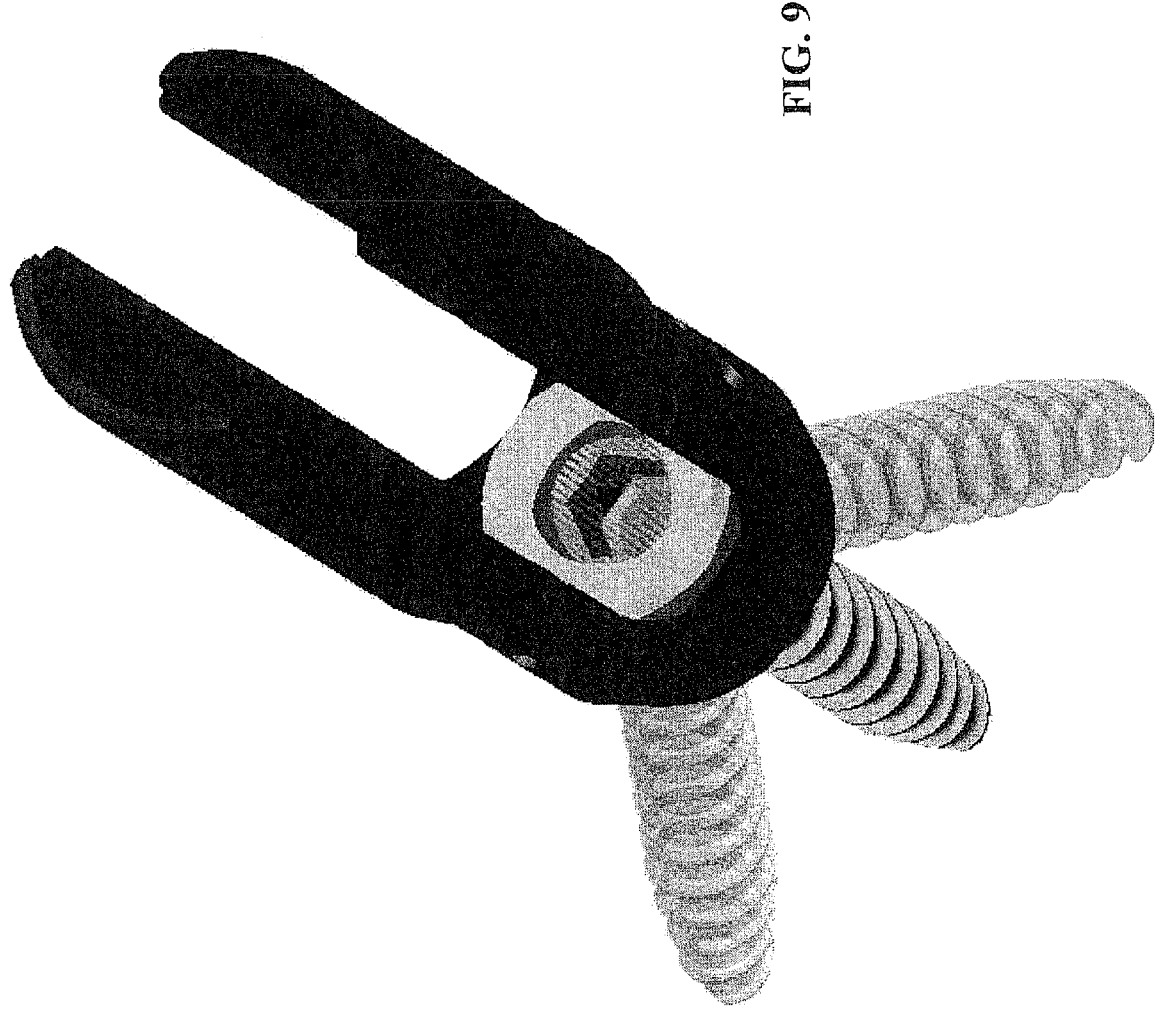
FIG. 9 is another embodiment of the screw system according to the present invention.
Figure 10:
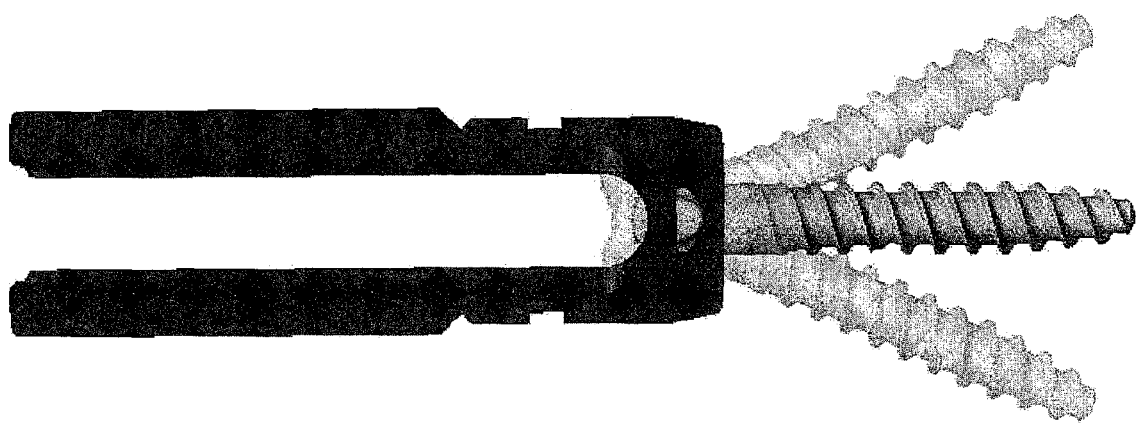
FIG. 10 is yet another view of the embodiment illustrated in FIG. 9.

FIGS. 9 and 10 illustrate two additional embodiments of the present invention. In these illustrations, the housing is providing with elongated sidewalls. These sidewalls are configured with indentations that can be removed by applying pressure once the fastener is positioned within the bony elements of the spine using a removal instrument. FIGS. 9 and 10 also illustrate the motion of the shaft portion of the fastener in one plane according to one aspect of the invention.

While many features of the invention will be described more fully below with reference to the accompanying drawings illustrating several embodiment of the invention, it is to be understood at the outset that skilled artisans having the benefit of this disclosure may recognize further variation or modifications of the invention that may also achieve the functions and results of this invention. Accordingly, the descriptions which follow are to be understood as illustrative and exemplary of specific structures, aspects, and features within the broad scope of the invention and not as limiting of such broad scope.

What is claimed is:

1. A spinal stabilization system for surgical implantation in the spine comprising:
   a bone fastener, the bone fastener having a head portion and a shaft portion;
   a housing having a recess defined by sidewalls and the housing having bottom portion with an opening for receiving the head portion of the bone fastener;
   a seating element disposed within the housing and positioned over the head portion of the bone fastener;
   an elongate rod positioned on the seating element within the recess of the housing;
   a cap capable of engaging with a top portion of the housing and capturing the elongate rod within the recess of the housing when the cap is rotated;
   wherein the head portion of the bone fastener is provided with at least one protrusion that is seated within an aperture on at least one of the sidewalls of the housing,
   wherein the head portion of the bone fastener is articulatable with respect to the housing and seating element,
   wherein the opening in the bottom portion of the bone fastener is rectangular and the head portion of the fastener is configured with a curved top and a quadrangluar base,
   wherein the top of the head portion is disposed within a bottom section of the seating element,
   wherein the top of the bone fastener is textured,
   wherein the bone fastener articulates with respect to the housing in a single plane, and the bone fastener is in a locked position when the elongate rod is compressed on the seating element,
   wherein the at least one protrusion fitted within the aperture forms a hinge.

2. The spine stabilization system of claim 1, wherein the top of the head portion is cylindrical.

3. The spine stabilization system of claim 1, wherein the top of the bone fastener has a plurality of grooves.

4. The spine stabilization system of claim 1, wherein the bottom section of the seating element is grooved.

5. The spine stabilization system of claim 4, wherein the grooves on the top of the bone fastener and the bottom section of the seating element mate.

6. The spine stabilization system of claim 1, wherein seating element is curved.

* * * * *